United States Patent
Moore et al.

(10) Patent No.: US 6,440,906 B1
(45) Date of Patent: *Aug. 27, 2002

(54) SOLVENT FOR LIQUID INGREDIENTS TO BE USED IN EFFERVESCENT PRODUCTS

(75) Inventors: Ryan Giffin Moore, Lilburn; Hilton G. Dawson, Canton; Richard A. DeSenna, Duluth; Kenneth Scott Wiley, Oakwood, all of GA (US)

(73) Assignee: Chemlink Laboratories, LLC, Kennesaw, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/813,620

(22) Filed: Mar. 21, 2001

Related U.S. Application Data

(63) Continuation-in-part of application No. 09/803,130, filed on Mar. 9, 2001.
(60) Provisional application No. 60/245,850, filed on Nov. 3, 2000, and provisional application No. 60/245,614, filed on Nov. 3, 2000.

(51) Int. Cl.$^7$ .............................. C11D 3/39; C11D 3/43
(52) U.S. Cl. ................. 510/117; 510/116; 510/141; 510/276; 510/278; 510/309; 510/445; 510/446
(58) Field of Search ................. 510/116, 117, 510/141, 276, 278, 309, 445, 446

(56) References Cited

U.S. PATENT DOCUMENTS

| | | | | |
|---|---|---|---|---|
| 4,409,118 A | | 10/1983 | Eoga ............................ | 252/99 |
| 4,412,978 A | | 11/1983 | Ertle ........................... | 423/279 |
| 4,518,520 A | | 5/1985 | Eoga ...................... | 252/174.23 |
| 4,687,662 A | | 8/1987 | Schobel ....................... | 424/44 |
| 4,772,412 A | * | 9/1988 | Green et al. .................. | 252/96 |
| RE32,771 E | | 10/1988 | Eoga ........................... | 252/99 |
| 4,857,224 A | | 8/1989 | Eoga ........................... | 252/99 |
| 5,354,510 A | | 10/1994 | Vanlerberghe et al. ...... | 252/548 |
| 5,384,062 A | | 1/1995 | Eoga et al. ................... | 252/99 |
| 5,476,607 A | | 12/1995 | Eoga et al. ................... | 252/99 |
| 5,486,304 A | | 1/1996 | Eoga et al. ................... | 252/99 |
| 6,071,539 A | * | 6/2000 | Robinson et al. ............ | 424/466 |
| 6,083,488 A | | 7/2000 | Riccobono et al. ........... | 424/44 |
| 6,239,093 B1 | | 5/2001 | Foley et al. ................. | 510/352 |

FOREIGN PATENT DOCUMENTS

| | | | | |
|---|---|---|---|---|
| EP | 0053859 A1 | 12/1981 | ...................... | 3/39 |
| EP | 53859 | * 6/1982 | | |
| EP | 0217454 B1 | 9/1986 | ...................... | 15/12 |
| FR | 2417470 | 2/1978 | ...................... | 15/12 |
| WO | WO99/58444 | 5/1999 | ............ | C01B/15/00 |
| WO | WO99/58632 | 5/1999 | ............ | C11D/3/00 |
| WO | 99/58444 | * 11/1999 | | |

OTHER PUBLICATIONS

U.S. patent application, Carrier for Liquid Ingredients to be used in Effervescent Products, Ser. No. 09/813,540, filed Mar. 21, 2001.

* cited by examiner

*Primary Examiner*—Charles Boyer
(74) *Attorney, Agent, or Firm*—James W. Kayden; Thomas, Kayden, Horstemeyer & Risley, LLP

(57) ABSTRACT

An effervescent compound is disclosed which includes a solvent and an effervescent system. The solvent may be both hydrophilic and have low solubility with organic effervescent ingredients. The solvent may include a glycol ether, for example, but not limited to, 2-butoxyethanol. The effervescent system used in the effervescent compound may be, for example, but is not limited to, expanded sodium perborate or a mixture of sodium bicarbonate, sodium carbonate, and an acid. The effervescent compound may further include any one, or all, or any combination of the following ingredients: surfactants, bleaching compositions, anti-redeposition agents, binders, lubricants, colors, fragrances, and/or optical brighteners. Also disclosed is a method for making an effervescent compound, including the steps of providing a solvent, providing an effervescent system in powder form, and mixing the solvent with the effervescent system, thereby producing a free-flowing effervescent compound. The method disclosed may also include the steps of compressing the effervescent compound, and then forming either granules or a tablet.

35 Claims, No Drawings

SOLVENT FOR LIQUID INGREDIENTS TO BE USED IN EFFERVESCENT PRODUCTS

CLAIM OF PRIORITY AND CROSS-REFERENCE TO RELATED APPLICATIONS

This application is a continuation-in-part of co-pending U.S. patent application entitled, "Solvent for Liquid Ingredients to Be Used in Effervescent Products," filed on Mar. 9, 2001, and accorded Ser. No. 09/803,130, and claims priority to co-pending U.S. provisional patent application entitled "Solvent for Liquid Ingredients to be Used in Effervescent Products" filed on Nov. 3, 2000 and accorded Ser. No. 60/245,850, which is entirely incorporated herein by reference. This application is related to co-pending U.S. provisional patent application entitled "Carrier for Liquid Ingredients to be Used in Effervescent Products" filed on Nov. 3, 2000 and accorded Ser. No. 60/245,614, which is entirely incorporated herein by reference.

TECHNICAL FIELD

The present invention is generally related to use of a solvent for liquid ingredients to be used in cleaning products, and, more particularly, is related to a method for producing effervescing products from liquid ingredients.

BACKGROUND OF THE INVENTION

One major limitation in effervescent cleaning, disinfecting, or other products was the amount and type of active ingredients that could be incorporated into effervescent formulations. Generally, less than 25% by weight of the tablet was available for active ingredients. Typically. surfactants, e.g., anionic, nonionic, cationic and amphoteric, could be used at no more than 5% of the formulas because these ingredients reduced the storage stability of carbonate-based effervescent products, made conventional granulation or tableting difficult or impossible and dramatically increased the dissolution time of the resulting products. Many surfactants are available only as liquids containing water or alcohol and could not be employed at any useful level in non-effervescent formulas. Generally, solvents were incompatible with effervescent products. They were either very hydrophobic and were incompatible with aqueous systems or are sufficiently hydrophilic to initiate the effervescent reaction, thus making the product unstable. Previously, solvents were primarily used in effervescent tablet production for wet granulation and had to be evaporated off to produce the finished tablet.

As noted previously, in typical effervescent tablets, less than 25% by weight of the tablet was usually available for ingredients other than the effervescent system. For example, although up to 75% by weight of the tablet weight could be a binder, 10% to 25% was typically used. The effervescent system typically accounted for up to 50% of the tablets. It should be noted that the more of the effervescent system that was used, the quicker the tablet dissolved. Lubricants, which help in tablet production, comprise up to 10% by weight of the tablet. Fragrance and color make up less than 2% of the tablet. It was found that high levels of fragrance adversely affected tablet stability, dissolution, hardness and tablet production.

Thus, a heretofore unaddressed need exists in the industry to address the aforementioned deficiencies and inadequacies.

SUMMARY OF THE INVENTION

The present invention provides both an effervescent compound and a method for making an effervescent compound. Briefly described, the effervescent compound includes both a solvent and an effervescent system. The solvent of the effervescent compound is compatible with the effervescent system and may be both hydrophilic and have low solubility with effervescent ingredients. In general terms, the solvent may include alcohols, glycols or glycol ethers. The effervescent system of the effervescent compound may include either expanded anhydrous sodium perborate and/or a mixture of an acid and one or more of sodium bicarbonate, sodium carbonate, potassium bicarbonate and potassium carbonate. The compound may further include any one, all, or any combination of the following ingredients: a surfactant, bleaching composition, an anti-redeposition agent, a binder, a lubricant, a color, a fragrance, and/or an optical brightener.

The present invention can also be viewed as providing a method for making an effervescent compound. In this regard, the method can be broadly summarized by the following steps: providing a solvent; providing an effervescent system in powder form; and mixing the solvent with the effervescent system, thereby producing a free-flowing effervescent compound. Alternative embodiments of the present invention include the further steps of compressing the effervescent compound and forming granules of the effervescent compound. Further, in an alternative embodiment, the method may also include compressing the effervescent compound and forming a tablet from the effervescent compound.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

DETAILED DESCRIPTION OF THE PREFERRED EMBODIMENT

The present invention is able to solve the aforementioned deficiencies and inadequacies by using in an effervescent compound a solvent that is compatible with effervescent ingredients. Thus, the present invention includes a solvent in effervescent compounds in the form of tablets, granules or powders. The solvent of the present invention can be used to dissolve many active ingredients, which results in an improved solubility rate for the effervescent compound. In various embodiments of the present invention, many different solvents may be used. In the preferred embodiment, the solvent is sufficiently hydrophilic to be used in aqueous products, but does not initiate an effervescent reaction with the effervescent ingredients of the effervescent compound. Preferably, the solvent can also be used as an active ingredient in the effervescent compound. In one embodiment of the present invention, the solvent includes a glycol ether. In the preferred embodiment, the solvent comprises, for example, but is not limited to, 2-butoxyethanol. Solvents of this type used in the present invention do not adversely affect either the physical or chemical stability of the effervescent compound, and also provide the possibility of tabulating or granulating the effervescent compound.

The effervescent compound including the solvent of the present invention may be formed into a tablet. "Tablet" means both tablets and the granular form of effervescent products. "Granular" means uniform-sized compressed mixtures. These tablets are shelf stable and have good physical properties. For example, but not limited to these physical characteristics, the tablets may be hard; non-friable; of minimum size, both in weight and dimension for the application; and have an increased dissolution rate over tablets not made with the solvent of the present invention.

The effervescent system of the present invention may be, for example, but is not limited to, expanded anhydrous sodium perborate (ESPB), and/or a mixture of an acid and one or more of sodium bicarbonate, sodium carbonate, potassium bicarbonate and potassium carbonate. Typically, the effervescent system is in a powdered form. If ESPB is used as the effervescent system, the solvent may be present in the effervescent compound of the present invention in an amount up to approximately 50% by weight of the composition. If, however, a carbonate/acid effervescent system is used the solvent may be used up to an amount of approximately 35% by weight of the effervescent compound. If the solvent is used alone with the effervescent system, and no other ingredients are added, the solvent itself may act as a cleaning ingredient, including, for example, but not limited to, a "degreaser," which is a compound that will render oils miscible with water.

Many other ingredients, preferably in powder form, may also be added to the solvent and included in the effervescent compound. Desirable, but not necessary, characteristics of these ingredients include being compressible, free-flowing, concentrated, and not being sticky. These ingredients include, but are not limited to, the following: surfactants, bleaching compositions, optical brighteners, anti-redeposition agents, binders, lubricants, colors, and/or fragrances. These ingredients may be used in any combination, depending on the application sought for the effervescent compound of the present invention.

Examples of surfactants that may be added to the effervescent compound include, but are not limited to: synthetic anionic surfactants which are generally water-soluble alkali metal salts of organic sulfates and sulfonates, non-ionic surfactants which are generally the reaction products of alkylene oxide with alkyl phenol or primary or secondary alcohols or are amine oxides, phosphine oxides or dialkyl sulphoxides, amphoteric or zwitterionic surfactants and/or soaps. Examples of the bleaching composition that may be used include, but are not limited to, chlorinated isocyanurates, perborate hydrates, persulfates or percarbonates. Examples of the anti-redeposition agent include, but are not limited to, acrylates and cellulose derivatives. The binder used in the effervescent compound may include, for example, but is not limited to, starch and starch derivatives, cellulose and cellulose derivatives., carbohydrate gums, sugars, resins, proteins and inorganic salts. Examples of the lubricant include, but are not limited to sodium benzoate, sodium stearate, magnesium stearate, aluminum stearate, stearic acid, mineral oil and polyethylene glycol.

There are several examples of effervescent products that may be made with the solvent of the present invention, for example, including, but not limited to, a carpet cleaner, a glass cleaner, a laundry detergent, a hard surface cleaner/disinfectant, and an all-purpose cleaner. The various cleaners and detergents that may be made from the solvent of the present invention may be in tablet, granular, or powder form. When in tablet form, the various cleaners and detergents may be dissolved in a liquid solution to form a cleaning solution. The liquid solution in the preferred embodiment is water, but may also be any liquid suitable for dissolving and using the cleaner of the present invention, including for example, but not limited to, an alcohol, e.g., low molecular weight alcohols such methanol, propanol and isopropanol; an aldehyde, e.g., formaldehyde or acetaldehyde; or a ketone, e.g., a low molecular weight ketone such as acetone, methyl ethyl ketone, methyl isopropyl ketone, or methyl propyl ketone. Table 1 below gives exemplary products in the form of detergent or cleaner tablets that may be made with the solvent and the present invention, and the volume of liquid in which the respective cleaner may be dissolved to form a cleaning solution.

TABLE 1

Exemplary Products and Dilution Volumes

| Product | Approximate Product Weight (g) | Approximate Dilution Volume |
|---|---|---|
| laundry detergent | 30–120 | 12 gallon |
| carpet cleaner | 25–100 | 1 gallon |
| all-purpose cleaner | 10–40 | 1 liter |
| glass cleaner | 7–30 | 1 liter |

The above weight and volume ranges are merely possible embodiments of the cleaners or detergents of the present invention, and other possible weight ranges would be known by those skilled in the art based on the disclosure herein. For example, in each example, dosages less than specified could be used with reduced performance and higher doses could also be used, but may result in wasting of the cleaning product. The preferred embodiment of each example given above follows: for the laundry detergent, approximately two 30-gram tablets or one sixty-gram tablet is used in a typical wash load of approximately 12 gallons; for the carpet cleaner, approximate 50 grams of cleaner is dissolved in approximately one gallon of liquid solution; for the all-purpose cleaner, approximately 19 grams of cleaner is dissolved in one liter of liquid solution; for the glass cleaner, approximately 15 grams of cleaner is dissolved in approximately one liter of liquid solution.

The effervescent carpet cleaner that may be made from the carrier of the present invention can include liquid ingredients in an amount up to 50% by weight of the carpet cleaner. For example, but not limited to, approximately 23% by weight of the composition may be a solvent, which had not previously been accomplished in previous carpet cleaners. Further, the exemplary embodiment of the carpet cleaner using the carrier of the present invention man include surfactant in an amount, for example, but not limited to, approximately 20% by weight of the composition, which is four times the usual concentration of surfactant that has been used heretofore in effervescent cleaners. Additionally, this exemplary embodiment of the carpet cleaner may include a fragrance in an amount, for example, but not limited to, approximately 3% by weight of the composition. Thus, this exemplary carpet cleaner may include liquid ingredients in an amount, for example, but not limited to, 46% by weight of the effervescent cleaner, which is five to ten times the amount that was previously possible for the liquid concentration. Further, the carpet cleaner tablet made using the carrier of the present invention has a dissolution time of less than five minutes at 40° C.

Another example of a cleaner that may be produced using the carrier of the present invention is a glass cleaner. The glass cleaner may be made in, for example, but not limited to, granular or tablet form. The glass cleaner may incorporate liquid ingredients in an amount up to 50% by weight of the glass cleaner. In an exemplary embodiment, the glass cleaner may include, for example, but is not limited to, 30% solvent by weight of the composition, which had not previously been accomplished in conventional effervescent products. Further, this exemplary glass cleaner may include, for example, but is not limited to, 5% by weight surfactant, and therefore rendering the liquid ingredients in an amount, for example, but not limited to, 35% by weight of the composition. Further, the glass cleaner also has a dissolution time of less than approximately five minutes at approximately 40° C.

Another example of a possible cleaner that may be produced using the carrier of the present invention is a laundry detergent. This laundry detergent may include liquid ingredients in an amount up to 50% by weight of the laundry detergent. In an exemplary embodiment of the laundry detergent, the liquid surfactant may be present in an amount, for example, but not limited to, 24% by weight of the composition, an amount that had not previously been accomplished in effervescent cleaners. This exemplary laundry detergent may also include, for example, but not limited to, 5% fragrance, which is two to five times the amount that has been used in typical effervescent formulas. The laundry detergent has a dissolution time of less than five minutes at 20° C.

Another example of a possible cleaner that may be produced using the carrier of the present invention is a hard surface cleaner/disinfectant. This hard surface cleaner may include liquid ingredients in an amount up to 50% by weight of the hard surface cleaner/disinfectant. In an exemplary embodiment of the hard surface cleaner, the solvent may be present in an amount, for example, but not limited to, 24% by weight of the composition, an amount that had not previously been accomplished in conventional hard surface cleaners. This exemplary hard surface cleaner may also include, for example, but not limited to, 15% quaternary ammonium salts (quat), which is five times the amount that has been used in conventional effervescent tablets. This exemplary hard surface cleaner may additionally include surfactants in an amount, for example, but not limited to, 5% by weight of the composition, and liquid active ingredients in an amount, for example, but not limited to, approximately 39% by weight of the composition. The hard surface cleaner also has a dissolution time of less than approximately five minutes at approximately 40° C.

Also included within the scope of the present invention is a method for making an effervescent compound that includes the steps of providing a solvent, providing an effervescent system in powder form, and mixing the solvent with the effervescent system, thereby producing a free-flowing effervescent compound. The method may also include the steps of compressing the compound and forming either granules or a tablet of the effervescent compound. The solvent used in the step of providing a solvent is preferably both hydrophilic and has low solubility with effervescent ingredients. The solvent may be, for example, but is not limited to, a glycol ether, e.g., 2-butoxyethanol. The effervescent system used in the step of providing an effervescent system in powder form may be, for example, but is not limited to ESPB and/or a mixture of an acid and one or more of sodium bicarbonate, sodium carbonate, potassium bicarbonate and potassium carbonate. The method may further include the steps of providing other ingredients in a powder form that are to be mixed with the solvent and the effervescent system, thereby producing the effervescent compound. These ingredients include, but are not limited to, any one or any combination of the following: surfactants, bleaching compositions, optical brighteners, anti-redeposition agents, binders, lubricants, colors, and/or fragrances. If necessary, these ingredients may be mixed with or dissolved in the solvent of the present invention, and, if necessary, distilled to remove any water or low boiling-point alcohol or any liquid with a boiling point lower than that of the solvent. The resulting liquid can then be used in the effervescent compound. It should be noted that the resulting effervescent compound including the solvent of the present invention is stable and has good tableting and dissolution characteristics.

It should be emphasized that the above-described embodiments of the present invention, particularly, any "preferred" embodiments, are merely possible examples of implementations, and are merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. An effervescent composition comprising:
    a glycol ether solvent that is both hydrophilic and has low solubility with effervescent ingredients and comprises from approximately 23% up to approximately 50% by weight of the composition; and
    an effervescent system.

2. The composition of claim 1, wherein the solvent comprises 2-butoxyethanol.

3. The composition of claim 1, wherein the effervescent system comprises expanded anhydrous sodium perborate.

4. The composition of claim 1, wherein the effervescent system comprises:
    an acid and one or more of sodium bicarbonate, potassium bicarbonate, sodium carbonate and potassium carbonate.

5. The composition of claim 1, further comprising a bleaching composition.

6. The composition of claim 1, further comprising an anti-redeposition agent.

7. The composition of claim 1, further comprising a binder.

8. The composition of claim 1, further comprising a lubricant.

9. The composition of claim 1, further comprising a color.

10. The composition of claim 1, further comprising an optical brightener.

11. The composition of claim 1, further comprising a fragrance.

12. The composition of claim 1, further comprising a surfactant.

13. The composition of claim 12, wherein the surfactant is selected from the group consisting of: synthetic anionic surfactants which are water-soluble; alkali metal salts of organic sulfates and sulfonates; non-ionic surfactants which are the reaction products of alkylene oxide with alkyl phenol or primary or secondary alcohols; amine oxides; phosphine oxides; dialkyl sulphoxides; amphoteric surfactants; zwitterionic surfactants; and soaps.

14. A method for making an effervescent composition comprising the steps of:
    providing a glycol ether solvent that is both hydrophilic and has low solubility with effervescent ingredients in an amount from approximately 23% up to approximately 50% by weight of the compound;
    providing an effervescent system in powder form; and
    mixing the solvent with the effervescent system, thereby producing a free-flowing effervescent compound.

15. The method of claim 14, further comprising the steps of:
   compressing the effervescent composition; and
   forming granules of the effervescent composition.

16. The method of claim 14, further comprising the steps of:
   compressing the effervescent composition; and
   forming a tablet from the effervescent composition.

17. The method of claim 14, wherein the step of providing a solvent comprises providing 2-butoxyethanol.

18. The method of claim 14, wherein the step of providing an effervescent system comprises providing expanded anhydrous sodium perborate.

19. The method of claim 14, wherein the step of providing an effervescent system comprises providing an acid and one or more of sodium bicarbonate; sodium carbonate; potassium bicarbonate and potassium carbonate.

20. A detergent comprising:
   a glycol ether solvent that is both hydrophilic and has low solubility with effervescent ingredients and comprises from approximately 23% up to approximately 50% by weight of the detergent; and
   an effervescent system.

21. The detergent of claim 20, wherein the detergent is a laundry detergent.

22. The detergent of claim 20, wherein the detergent is granular.

23. The detergent of claim 20, wherein the detergent is a tablet.

24. A carpet cleaner comprising:
   a glycol ether liquid ingredient in an amount from approximately 23% up to approximately 50% by weight of the carpet cleaner; and
   an effervescent system.

25. The carpet cleaner of claim 24, wherein the carpet cleaner is granular.

26. The carpet cleaner of claim 24, wherein the carpet cleaner is a tablet.

27. The carpet cleaner of claim 24, wherein the cleaner is between approximately 25 and approximately 100 grams, and wherein the carpet cleaner further comprises approximately 1 gallon of water, to form a carpet cleaning solution.

28. An all-purpose cleaner comprising:
   a glycol ether solvent that is both hydrophilic and has low solubility with effervescent ingredients and comprises from approximately 23% up to approximately 50% by weight of the all-purpose cleaner; and
   an effervescent system.

29. The all-purpose cleaner of claim 28, wherein the all-purpose cleaner is granular.

30. The all-purpose cleaner of claim 28, wherein the all-purpose cleaner is a tablet.

31. The all-purpose cleaner of claim 28, wherein the all-purpose cleaner is between approximately 10 and approximately 40 grams, and wherein the all-purpose cleaner further comprises approximately 1 liter of water, to form an all-purpose cleaning solution.

32. A glass cleaner comprising:
   a glycol ether liquid ingredient in an amount from approximately 23% up to approximately 50% by weight of the glass cleaner; and
   an effervescent system.

33. The glass cleaner of claim 32, wherein the glass cleaner is granular.

34. The glass cleaner of claim 32, wherein the glass cleaner is a tablet.

35. The glass cleaner of claim 32, wherein the glass cleaner is between approximately 7 and approximately 30 grams, and wherein the glass cleaner further comprises approximately 1 liter of water, to form a glass cleaning solution.

* * * * *